United States Patent [19]

George

[11] Patent Number: 4,861,337
[45] Date of Patent: Aug. 29, 1989

[54] COLLAPSIBLE URETHRAL CATHETER

[75] Inventor: Robert D. George, Lake Saint Louis, Mo.

[73] Assignee: Sherwood Medical Company, St. Louis, Mo.

[21] Appl. No.: 163,264

[22] Filed: Mar. 2, 1988

[51] Int. Cl.⁴ .................................. A61M 25/00
[52] U.S. Cl. ............................ 604/96; 128/344
[58] Field of Search .................... 604/96–103, 604/247, 256, 280; 128/344, 348.1

[56] References Cited

U.S. PATENT DOCUMENTS

| | | | |
|---|---|---|---|
| 2,819,718 | 1/1958 | Goldman | 604/96 |
| 3,331,371 | 7/1967 | Rocchi et al. | 604/96 |
| 3,605,749 | 9/1971 | Heimlich | 604/247 |
| 3,832,253 | 8/1974 | De Palma et al. | 156/86 |
| 3,865,666 | 2/1975 | Shoney | 156/245 |
| 4,178,937 | 12/1979 | Taylor et al. | 128/349 B |
| 4,198,963 | 4/1980 | Barkalow et al. | 128/53 |
| 4,210,478 | 7/1980 | Shoney | 156/242 |
| 4,222,384 | 9/1980 | Birtwell | 128/349 B |
| 4,276,874 | 7/1981 | Wolvek et al. | 604/96 X |
| 4,445,890 | 5/1984 | Patel | 604/103 |
| 4,445,891 | 5/1984 | Patel | 604/103 |
| 4,447,228 | 5/1984 | Patel | 604/103 |
| 4,553,959 | 11/1985 | Hickey et al. | 604/96 |
| 4,680,029 | 7/1987 | Ranford et al. | 604/280 |

Primary Examiner—Dalton L. Truluck
Attorney, Agent, or Firm—Stanley N. Garber; Andrew J. Beck; Charles Smith, Jr.

[57] ABSTRACT

A collapsible and flexible urethral drainage catheter having a flexible tubular body portion containing a drainage lumen and an inflation lumen and having a distal tip portion with a flexibility different from the body portion with a distal end closed by an elongated cylindrical plug member sealed thereto having a segment of the wall thereof adapted when inserted into the distal end of the body portion to mate in intimate contact with the inner wall of the body portion and extending a sufficient distance into the body portion to stiffen the distal tip portion thereof, said drainage lumen communicating with drain ports in the elongated plug member and the distal tip portion of said body member and said inflation lumen communicating with an inflation cuff surrounding a portion of said distal tip portion of the body member.

17 Claims, 2 Drawing Sheets

COLLAPSIBLE URETHRAL CATHETER

The present invention is directed to collapsible or very flexible urethral catheters, and more particularly, to such collapsible urethral catheters having secure and leak-proof connections between the constituent parts thereof.

Certain requirements have been recognized with drainage devices such as urethral catheters designed for insertion and retention in the urethra for draining the bladders of patients. Among these requirements is the need for sufficient stiffness in the distal ends of such catheters to enable them to be relatively easily inserted into the patient through the urethral canal and to enter and be anchored in the patient's bladder. Also, maintaining a relatively small diameter throughout and a relatively flexible and collapsible main or trailing portion thereof are important for patient comfort and improved patient retention. Urethral catheters having inflatable balloon sections which serve when inflated to hold the distal ends of such catheters in fixed position inside the bladder have been developed and used in the past. Also, drainage catheters having distal ends or tips comprised of relatively stiff materials such as those displaying a lower modulus of elasticity than the balloon portion and the trailing portion of the catheter have also been used in the past.

Catheters used to drain internal organs, for example, Foley catheters used for bladder catheterization generally have an inflatable cuff or balloon near their distal ends. When such a catheter is fully inserted into the patient's urethra, the distal end and the uninflated balloon enters the bladder. Thereafter, the balloon is inflated to prevent the catheter from inadvertently moving and coming out of the bladder. Catheters with balloons, such as Foley catheters, usually have an auxiliary or inflation lumen formed in the sidewall of the catheter tube which communicates with the balloon. Usually, an inflation tube is connected to the inflation lumen near the proximal end of the catheter and a check valve is provided near the proximal end of the inflation tube to prevent loss of inflation pressure. In the typical Foley catheter the proximal end is provided with a separate inflation tube having a connection to the inflation lumen, and the drain tube is attached to the main lumen in the catheter. These tubes frequently are embodied in a form having a Y-shape, both portions of which are usually made of a relatively soft and flexible plastic material such as a latex, polyvinyl chloride, polyurethane or polysilicone.

With all known prior catheter designs special problems have been found in providing reliable production runs of uniform high quality catheters, particularly where there are sealed or cemented connections between the different sections. For example, it is often difficult to assure that a cemented connection or joint is securely and adequately sealed and such is essential for successful emplacement and use of such urethral drainage catheters. Difficulties have also been encountered in forming securely sealed or cemented connections while maintaining fully open and unobstructed lumens. Urethral catheters of the balloon type require an inflation lumen to provide means for admitting and withdrawing air or other fluid from the balloon portion during inflation and deflation thereof. Additionally, the main lumen, generally of greater diameter, is provided for draining the patient's bladder. The need for a relatively stiff distal tip portion as well as provision of an inflatable balloon portion with a trailing portion for the tubular catheter that is more flexible than the distal tip portion has posed problems in the successful design and manufacture of such devices. An additional consideration is the need to provide a Y-shaped proximal end portion which remains outside the patient's body and yet provides access including ingress and egress to the main and to the inflation lumens. The Y-shaped proximal end portion can be formed from a flexible material or, if desired, it can be formed from a stiffer material. Generally, this part is made from a flexible material but with somewhat thicker walls that provide a more stable construction for the connections thereto required for a collection tube and/or device and for a syringe used for producing the pressure required for inflation and deflation of the balloon portion.

Each individual portion of the completed Foley catheter must be securely sealed to the other portions connected thereto so as to assure leak-free operation as well as free and unobstructed communication through the inflation and main lumens. Generally, such sealed connections or joints are made by cementing and/or heat sealing the respective connected portions of the catheter. Such connections or joints have frequently been found to be prone to develop fluid leaks especially if they are not additionally sheathed with a sealed outer layer, and where a sheathing layer is used it complicates the construction and adds to the size and inflexibility of the catheter. The present invention is directed to the solution of these problems and teaches the construction of an improved urethral catheter.

It is therefore a principal object of the present invention to provide a drainage catheter of the above-described type wherein the requirements mentioned above are incorporated in the construction.

Another object is to provide a catheter such as a Foley catheter having a tip portion of different flexibility than the trailing portion thereof and improved leak-proof means forming the connections between the portions.

Another object is to improve the construction of devices that require flexible tubular connections including devices such as medical drainage catheters and the like.

Another object is to provide improved means for connecting different portions of a catheter which means assure a secure leak-proof construction.

Another object is to provide a catheter construction that is relatively easy to install and which is more comfortable for the patient.

Another object is to provide improved means for connecting the different portions of a catheter which means assures unobstructed communication through the inflation and drainage lumens therein.

Another object is to provide a better and less expensive way to manufacture medical drainage catheters.

Another object is to simplify the construction of the connections used between the flexible tubular members of medical drainage catheters.

In accordance with one embodiment of the present invention, a medical drainage catheter is provided which has a flexible tubular body portion containing a drainage lumen and at least one other secondary lumen, a tip portion having a flexibility that is different from the body portion, a closed distal end including a cylindrical plug portion having a segment of the wall thereof adapted to mate with and be inserted into the distal end of the body portion in intimate contact with the inner wall of the tubular body portion and extending a sufficient distance into the tubular body to stiffen the distal end portion thereof so as to make it easy to insert the catheter and yet provide a sealed secondary lumen that is continuous and uninterrupted in the catheter.

These and other objects and advantages of the present invention will become apparent to those skilled in the art after considering the following detailed specification in conjunction with the accompanying drawings.

DETAILED DESCRIPTION OF THE PREFERRED EMBODIMENTS

Figure 1:
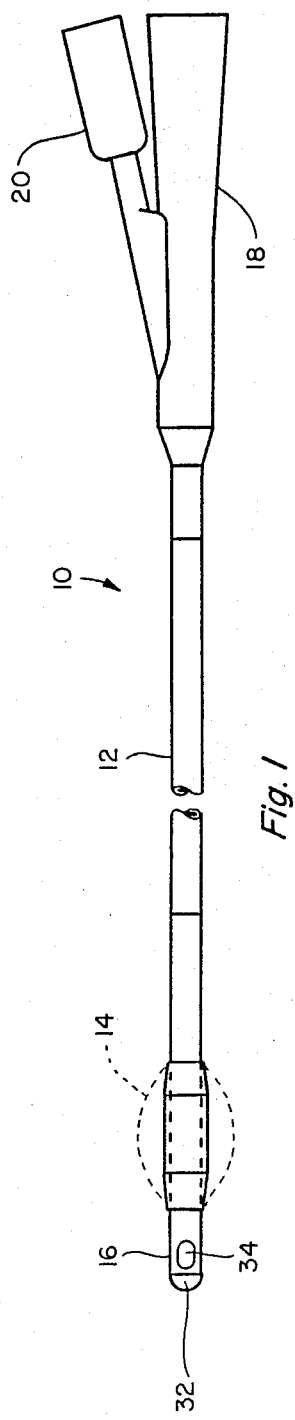
FIG. 1 is a side elevational view of a Foley catheter having incorporated therein a tip portion which includes an inserted plug constructed according to one embodiment of the present invention.
Figure 2:
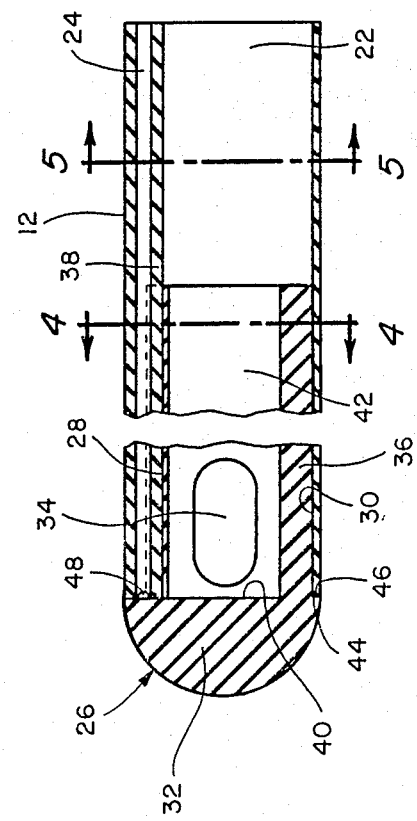
FIG. 2 is an enlarged and partially broken cross-sectional view taken through the center of the distal end portion only of the device of FIG. 1.

Referring to the drawings more particularly by reference numbers, number 10 in FIG. 1 refers to one embodiment of the medical device also known as an urethral Foley catheter adapted for insertion through the urethral canal into the bladder of a patient for draining urine therefrom. The catheter 10 includes a main catheter tube or body portion 12 having an expandable cuff or balloon member 14 surrounding a portion of the device near the distal end 16 of the device. The balloon member 14 can be radially outwardly expanded as shown in dotted outline in FIG. 1. The catheter also includes a main drainage connector portion 18 and an auxiliary connector portion 20 both located at the proximal end thereof. The portion 18 is for connection to a drainage tube where urine is collected in a container or bag (not shown). The portion 20 is for connection to a fluid injection means or syringe (not shown) used for inflating or deflating the balloon 14. As seen in FIG. 2, catheter 10 has a longitudinally extending tubular main or drainage lumen or passageway 22 and at least one auxiliary or inflation lumen or passageway 24. The proximal end of inflation lumen 24 is connected to communicate with the auxiliary connector portion 20 and may include a check valve (not shown) which prevents the balloon 14 from deflating when the device is installed and inflated.

Figure 3:
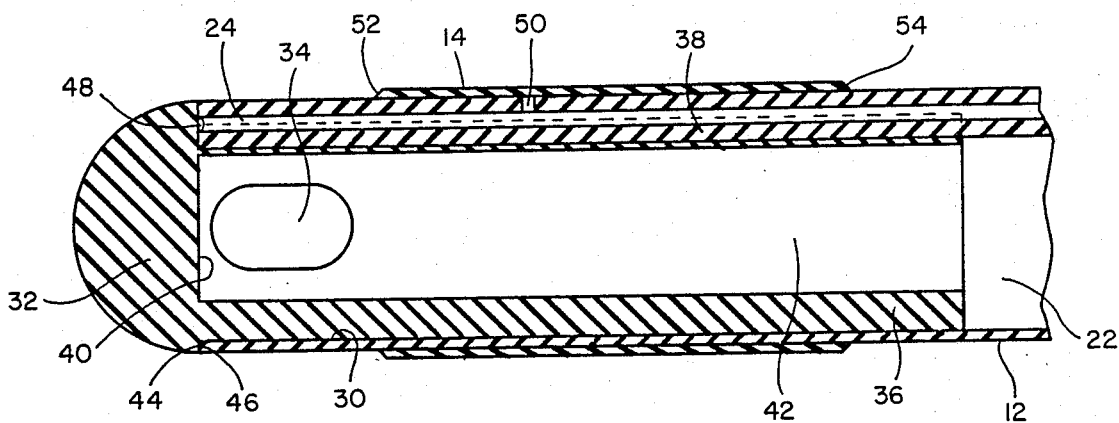
FIG. 3 is an enlarged cross-sectional view similar to FIG. 2 showing the balloon member in place on the device.

Also as seen in FIG. 2, the distal or tip end portion 16 of the catheter 10 is of different and thicker construction overall than the portions extending therefrom to the proximal end of the catheter. This distal or tip end portion 16 includes an elongated plug 26 (FIG. 6) having a cylinder shaped wall 36 defining a central bore 42 and with a cut-out or trough 28 formed in the outer surface of wall 36, and sized to snugly receive and mate with the interior surface 30 of the tubular body 12 as will be more fully explained. The plug 26 is included to stiffen the end portion 16 of the catheter 10 to make it easier to insert into position for use. The plug 26 is made long enough so that its open proximal end when inserted into the distal end 16 of body portion 12 will extend at least to and preferably somewhat beyond the proximal end 54 of the balloon portion 14, as shown in FIG. 3. The distal end of the plug 26 has a rounded relatively blunt distal tip portion 32 which is sized so that when the member 12 is installed on the plug 26 (or the plug is inserted therein) the end of the catheter 10 will have the smooth rounded form as shown. The rounded tip end portion 32 makes it relatively easy to install the catheter with minimum discomfort for the patient.

The plug 26 has one or more spaced side openings 34 (two being shown in FIGS. 4 and 6) through the wall 36 which openings 34 register with a like number of similarly positioned and shaped openings 35 formed through the tubular member 12. It is through these registered sets of openings 34 and 35 that the drainage from the bladder is able to enter the catheter 10.

Figure 4:
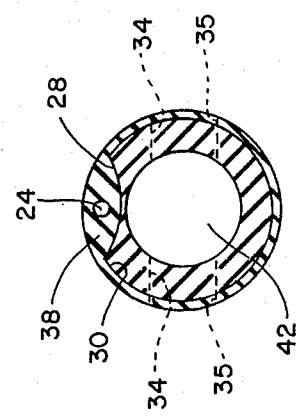
FIG. 4 is an enlarged cross-sectional view taken along line 4—4 of FIG. 2.
Figure 5:
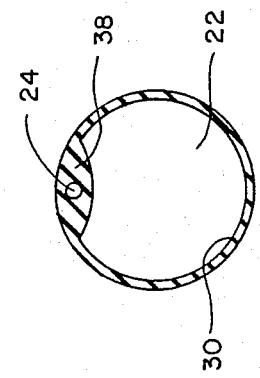
FIG. 5 is an enlarged cross-sectional view taken along line 5—5 of FIG. 2.
Figures 7, 8:
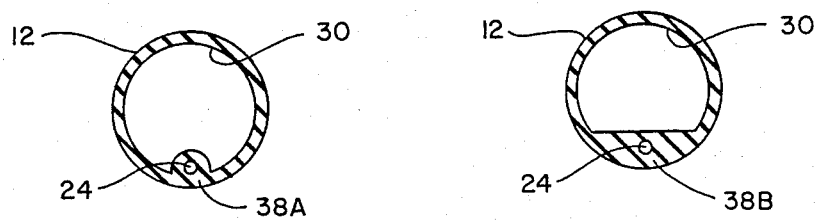
FIG. 7 is a cross-sectional view similar to FIG. 5 but showing another embodiment of the body portion of the subject catheter.
FIG. 8 is a cross-sectional view showing yet another embodiment of the body portion.
Figure 6:
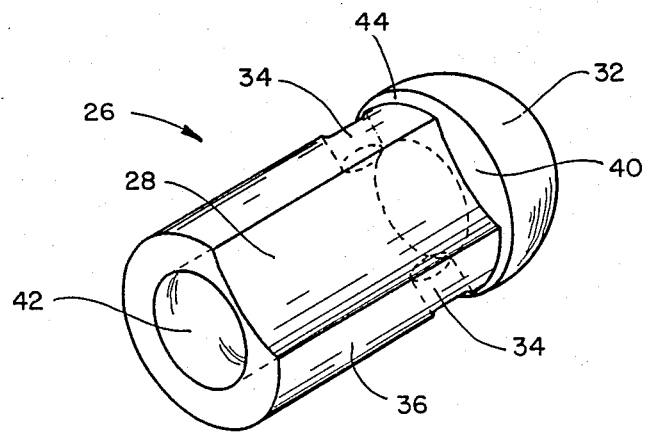
FIG. 6 is an enlarged perspective view of a plug used in the tip portion of the catheter shown in FIG. 1.

The tubular member 12 has a thickened wall portion 38 along one side thereof through which the inflation lumen 24 extends, and the thickened portion including the lumen 24 extend continuously along the length of the catheter. The plug 26 has a counterbore 42 therein which is closed at its distal end by plug wall 40 and is open at its opposite end for communication with the main passageway or drain lumen 22. The trough 28 is shown formed with a relatively wide arch as shown in FIGS. 4 and 6 to conform to the shape of the inner surface of the portion 38. It can also be formed with a smaller diameter arch as well as with a flat chord shape to conform to corresponding shapes 38A or 38B respectively of wall portion 38 as shown in FIGS. 7 and 8. Other shapes are also possible so long as the shape corresponds to the shape of the wall portion 38 and thus accommodates the inflation lumen 24.

The blunt or rounded shape of the distal plug tip 32 is formed to completely close the distal end of the member 12 including abutting the end of the thickened wall portion 38 (or 38A or 38B) thereof. This is done by providing radial shoulder 44 which extends all the way around the plug 26. Thus, when the plug 26 is positioned extending into the end of the tubular member 12 and bonded thereto the shoulder 44 will abut the end surface of the member 12. An adhesive such as adhesive 48 may be positioned between the shoulder 44 and the end of the member 12 to provide a positive leak-proof seal therebetween and to securely close the end of inflation lumen 24. The wall 36 of plug 26 is preferably likewise sealed to the interior wall 30 and to wall portion 38 of the member 12. The same parts can also be sealed by sonic welding or other techniques as well. The portion 38 in which the inflation lumen 24 is located is preferably formed continuously along the length of the member 12, and therefore there is generally no need for making connections therein, which is desirable since it avoids the possibility of leaks in such connections and simplifies the construction.

The various parts of the catheter 10 can be constructed of several different materials of which such catheters are generally made including materials such as of polyvinyl chloride, polyurethane, polysilicone and latex rubber.

The tubular member 12 can also have one or more radial extending ports or orifices such as port 50 (FIG. 3) which is centrally located axially between the ends of the balloon member 14. The port 50 communicates the space between the inner surface of the balloon 14 and the outer surface of the tubular member 12 with the inflation lumen 24. Both opposite ends 52 and 54 of the balloon 14 should be adhesively or otherwise sealed to the outer surface of the member 12 to form an airtight space. This is so that when air or other fluid pressure is introduced into the space therebetween by way of the lumen 24 it will be applied through the port 50 to force the balloon outwardly to enlarge its diameter as shown in dotted outline in FIG. 1. This is done to hold it in place as in a bladder and to prevent movement of the catheter 10 when installed in a patient. The end edges of balloon 14 are tapered as at 52 and 54 to form a smooth outer surface for the catheter and to facilitate insertion and removal. The end edges of the balloon 14 can be sealed to the member 12 by some means such as by adhesives or otherwise. The catheter portions 18 and 20 can be of conventional construction and are sealably connected at the proximal end of the body portion 12 to provide the main drainage passage or lumen and the necessary connections thereto and to provide the means for inflating the balloon 14 through the inflation lumen 24.

The dimensions of the subject catheter can be varied as desired including both as to length and as to diameter. A typical urethral Foley catheter in accordance with the present invention may have as long as a three inch stiffened distal end portion with a trailing flexible portion that may be as long as nine inches or even longer. The important thing is that the distal end portion of the catheter be stiff enough to be easily inserted into the bladder and yet long enough to reach the area to be drained and still have the opposite end accessible outside of the patient's body. This requires that the plug closing and stiffening the distal end portion thereof extend within the body portion of the catheter at least to a point underlying the proximal end of the balloon portion. The catheter should also be sized as to diameter to be easily inserted and still provide some clearance for inflation of the balloon portion to hold it in place without being uncomfortable to the patient. The stiffness of the plugged end portion makes these things possible. The simplicity of the present catheter construction and the fact that it is relatively easy to make and use are all important considerations and advantages therefor.

Thus there has been shown and described a novel catheter construction which fulfills all the objects and advantages sought therefor. It will be apparent to those skilled in the art, however, that many changes, modifications, variations and other uses and applications of the subject catheter construction are possible and contemplated. All such changes, modifications, variations and other uses and applications which do not depart from the spirit and scope of the invention are deemed to be covered by the invention which is limited only by the claims which follow.

What is claimed is:

1. A urethral catheter comprising an elongated tubular member of a relatively flexible material having inner and outer surfaces and adjacent but separated drainage and inflation passageways extending the length thereof, said tubular member having a distal end to be inserted into a bladder to be drained and a proximal opposite end, a separate plug member disposed into the tubular member from the distal end to stiffen the adjacent end portion of the tubular member to facilitate insertion of the catheter into a bladder, said plug member including a generally cylindrical body with a bore in communication with the drainage passageway, an inflatable bladder surrounding the tubular member over a portion of the length where the plug member is inserted, said inflatable bladder having opposed spaced end portions and means sealing the end portions to the tubular member to define an enclosed area therebetween, means in the tubular member communicating the inflation passageway with the enclosed area between the bladder and the tubular member, and communicating drain port means in the plug member and in the tubular member adjacent to the distal end of the tubular member for passing drainage fluid from the exterior of the catheter to the drainage passageway.

2. The urethral catheter of claim 1 wherein the tubular member has a thickened portion along one side extending the length thereof, the inflation passageway extending lengthwise through the thickened portion of the tubular member.

3. The urethral catheter of claim 2 wherein the plug member has an external contour that conforms with the contour of the inner surface of the thickened portion of the tubular member.

4. The urethral catheter of claim 1 wherein the tubular member is formed of a relatively soft flexible material and the plug member is formed of a relatively stiffer material.

5. The urethral catheter of claim 1 wherein said communicating drain port means include registering openings extending respectively through the sidewalls of the tubular member and the plug member.

6. A urethral catheter comprising an elongated tubular member of a flexible material having spaced distal and proximal ends and including a wall portion defining spaced drain and inflation lumens extending the length thereof, at least one drain opening through the tubular member adjacent to the distal end thereof, a separate tubular plug member including means closing one end thereof and having an outer surface shaped to intimately conform to the inner surface of the tubular member, said plug member being positioned in the tubular member and extending from the distal end thereof and having a rounded distal end surface and a shoulder opposite thereto for abutting the distal end of the tubular member to form a smooth and continuous outer surface therebetween, said plug member closing the distal end of the drain lumen and having a drain opening in the sidewall thereof communicating said drain opening in the tubular member with the drain lumen in the tubular member, means forming a radial outwardly extending orifice in the tubular member having one end in communication with the inflation lumen, and an annular sleeve formed of an inflatable material extending around the elongated tubular member in a position overlaying the other end of said orifice, said sleeve having opposite ends and means sealing the opposite ends of the sleeve to the tubular member, the space between the outer surface of the tubular member and the inner surface of the sleeve communicating with the inflation lumen through said orifice.

7. The catheter of claim 6 wherein the plug member is formed of a material that is less flexible than the tubular member.

8. The catheter of claim 6 including means for sealing the distal end of the tubular member to the shoulder formed on the plug member.

9. The catheter of claim 8 wherein the sealing means includes an adhesive, a portion of which closes the distal end of the inflation lumen.

10. The urethral catheter of claim 6 wherein the tubular member has a thickened wall portion extending lengthwise thereof and radially inwardly, the inflation passageway extending lengthwise through the thickened wall portion, and the plug member has an external contour that conforms with the contour of the thickened wall portion adjacent the distal end of the tubular member.

11. The urethral catheter of claim 6 wherein said drain opening in said tubular member extends through the sidewall thereof adjacent said drain opening on said plug member.

12. A Foley-type urethral drainage catheter having a relatively stiff distal end portion for insertion into a bladder to be drained comprising an elongate tubular member formed of a relatively flexible material including a wall member having inner and outer surfaces including a first inner surface forming a drainage lumen and a second inner surface forming an inflation lumen separated from the drainage lumen, a separate plug member positioned to extend from the distal end of the tubular member inwardly a predetermined distance to stiffen and support the end portion thereof, said plug member having a generally cylindrical portion with a closed end passageway formed therein in communication with the drainage lumen and a drain port in the sidewall thereof adjacent to the distal end portion of said tubular member, said tubular member having a drain port therethrough in communication with the closed end passageway, means sealably connecting the tubular member adjacent to the distal end thereof to the plug member, an inflatable bladder surrounding the tubular member over a portion of the length where the plug member is inserted, said inflatable bladder having spaced end edges and means sealing the end edges to the tubular member to define an enclosed area therebetween, and means in the tubular member communicating the inflation passageway with the enclosed area between the bladder and the tubular member.

13. The Foley-type catheter of claim 12 wherein the plug member is formed of a material that is relatively stiffer and less flexible than the tubular member.

14. The Foley-type catheter of claim 12 wherein the distal tip end portion of the plug member has ann annular shoulder abutting the distal end portion of the tubular member, and means for bonding between the shoulder and the distal end of the tubular member.

15. The Foley-type catheter of claim 12 wherein the distal end of the plug member is rounded.

16. The Foley-type catheter of claim 12 wherein the wall portion of the elongated flexible tubular member has a thickened portion formed extending along one side thereof, the inflation lumen including a passageway formed in the thickened portion of the wall member and extending the length thereof.

17. The Foley-type catheter of claim 16 wherein the plug member has an outer surface shaped to intimately conform to the shape of the inner surface of the tubular member.

* * * * *